United States Patent [19]

Mori

[11] Patent Number: 4,761,047
[45] Date of Patent: Aug. 2, 1988

[54] LIGHT RAYS RADIATION CLOTH FOR MEDICAL TREATMENT

[76] Inventor: Kei Mori, 3-16-3-501, Kaminoge, Setagaya-ku, Tokyo, Japan

[21] Appl. No.: 934,226

[22] Filed: Nov. 20, 1986

[30] Foreign Application Priority Data

Jan. 13, 1986 [JP] Japan ..................................... 61-4754

[51] Int. Cl.$^4$ .............................................. G02B 6/00
[52] U.S. Cl. ..................................... 350/96.1; 362/32; 350/96.27; 128/379; 2/DIG. 7
[58] Field of Search .................. 350/96.1, 96.15, 96.24, 350/96.21, 96.25, 96.27; 362/32; 2/1, DIG. 7; 128/24.1, 68.1, 82.1, 303.1, 379

[56] References Cited

U.S. PATENT DOCUMENTS

| | | | |
|---|---|---|---|
| 4,113,348 | 9/1978 | Yevick | 350/96.25 |
| 4,220,394 | 9/1980 | Tardy | 350/96.21 |
| 4,234,907 | 11/1980 | Daniel | 362/32 |
| 4,519,017 | 5/1985 | Daniel | 362/32 |

FOREIGN PATENT DOCUMENTS 57-17904  1/1982  Japan ............................... 350/96.27

*Primary Examiner*—John Lee
*Assistant Examiner*—John Ngo
*Attorney, Agent, or Firm*—Jordan and Hamburg

[57] ABSTRACT

A light rays radiation cloth for medical treatment comprises a flexible basic sheet plate, a large number of optical fibers arranged on one surface of the basic sheet plate, and a light rays connector for supplying light rays to the optical fibers. The optical fibers comprise respectively a light rays emitting portion for emitting the light rays transmitted through the optical fibers to the outside of the same at the half way points of the light rays transmitting route. The light rays are emitted almost uniformly from one surface of the basic sheet plate.

14 Claims, 3 Drawing Sheets

LIGHT RAYS RADIATION CLOTH FOR MEDICAL TREATMENT

BACKGROUND OF THE INVENTION

The present invention relates to a light rays radiation cloth for use in medical treatment, specifically, a light rays radiation cloth for administering various kinds of medical treatments by radiating light energy corresponding to the visible light rays component of solar rays onto the diseased part of a patient or executing beauty treatment or health promotion, etc. by radiating the same onto the surface of person's skin.

In recent years, a large number of persons have been suffering from such incurable diseases as arthritis, neuralgia and rheumatism, or from pain as a result of an injury or from an ill-defined disease. Furthermore, persons cannot avoid the effects of growing old on one's skin which progresses gradually from a comparatively young age. On the other hand, the present applicant has previously proposed to focus solar rays by the use of lenses or the like, to guide the same into an optical conductor, and to transmit them onto an optional desired place. Those solar rays transmitted in such a way are employed for use in illumination or for other similar purposes such as for cultivating plants, chlorella and the like. About the process, visible light rays, not containing ultraviolet and infrared rays, help to create a living body reaction which in turn promotes health and prevents a person's skin from growing old. Furthermore, those visible light rays help to relieve pain caused by arthritis, neuralgia, bedsores, rheumatism, injuries and bone fractures. Such beneficial results have been experienced and can be substantiated by the present applicant.

SUMMARY OF THE INVENTION

It is an object of the present invention to provide a light rays radiation cloth for use in medical treatment, for administering beauty treatments or for promoting good health.

It is another object of the present invention to provide a light rays radiation cloth for effectively radiating light rays, corresponding to the visible light rays of the sun, which contain no harmful components such as ultraviolet or infrared rays, onto the abdomen, the breasts, the legs or other portions of the human body.

It is another object of the present invention to provide a light rays radiation cloth for emitting the light rays from one surface thereof and for radiating the same onto a desired portion of the human body.

The above-mentioned features and other advantages of the present invention will be apparent from the following detailed description which goes with the accompanying drawings.

DESCRIPTION OF THE PREFERRED EMBODIMENTS

Figure 1:
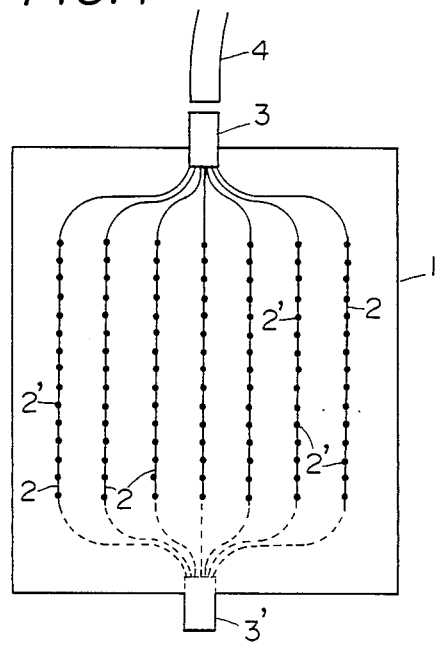
FIG. 1 is a construction view for explaining an embodiment of the present invention.

FIG. 1 is a plan view showing an embodiment of a light rays radiation cloth for medical treatment according to the present invention. In FIG. 1, 1 is a flexible basic sheet plate consisting of textile, knitted goods, or other unwoven cloth, 2 a large number of optical fibers arranged on one surface of the basic sheet plate 1, and 3 a light rays connected for supplying light rays to the respective optical fibers. The connector 3 can be connected with an optical conductor cable 4 through which solar rays collected by means of an automatic solar rays collecting and transmitting device, not shown in FIG. 1, are transmitted.

Figure 2:
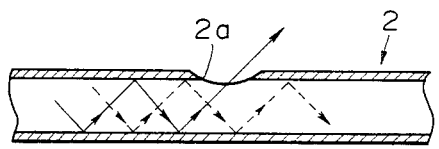
FIGS. 2(A) through 2(C) are cross-sectional views showing examples of a light rays emitting portion of the optical fiber.
Figure 2:
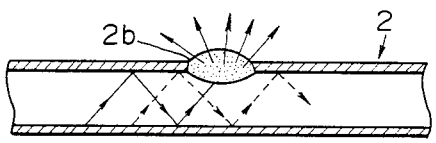
Figure 2:
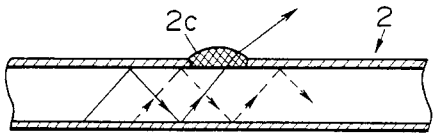

On the surface of the respective optical fibers 2 are provided or formed well-known optional desired means 2' for emitting outside of the optical fibers 2 the light rays transmitted therethrough. For instance, as shown in FIGS. 2(A) through 2(C), a depression 2a is formed on the core portion of the optical fiber 2 after removing a part of the clad layer portion thereof. Otherwise, a light rays dispersing body 2b is fittedly mounted on the depression 2a of the optical fiber 2, or a part of the clad layer portion thereof is removed and a transparent body 2c for causing the light rays to pass therethrough is bonded to the removed clad layer portion. As mentioned above, various optional desired means for emitting the light rays can be provided or formed on the surface of the optical fibers.

Or else, in the case of employing the optical fiber having no clad layer portion, a notch can be formed on the surface of the optical fiber, or a transparent substance for causing the light rays to pass therethrough, which has a refractive index differing from that of the optical fiber, can be bonded to the surface of the optical fiber for the purpose of radiating, outside of the optical fiber, the light rays transmitted therethrough, as already proposed in various ways by the present applicant.

An embodiment for guiding the light rays from only one end portion of the respective optical fiber has been described heretofore. However, as shown by 3' in FIG. 1, it will be possible to provide a light rays plug receptacle (consent) at both end portions of the optical fiber respectively in order to guide the light rays into the optical fiber from both end portions thereof. Furthermore, the surface of the basic sheet plate 1 on which the optical fibers 2 are arranged can be formed as a reflecting surface. In such a manner as mentioned above, the light rays can be radiated more and more effectively.

Figure 3:
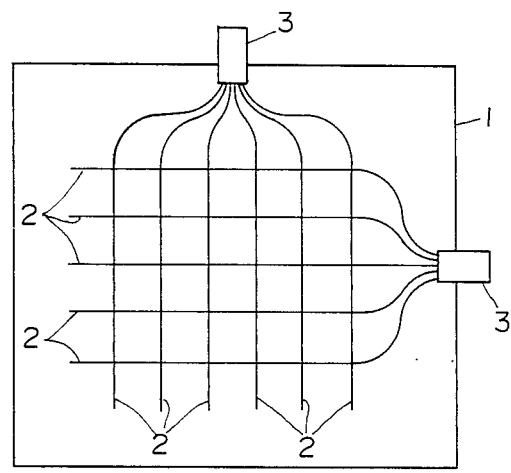
FIGS. 3 through 5 are construction views for explaining other embodiments of the present invention.

Furthermore, although an embodiment for arranging the optical fibers 2 only in one direction has been described heretofore, those optical fibers can be arranged so as to intersect each other in lengthwise and lateral directions, as shown in another embodiment of FIG. 3. In such a manner as mentioned above, it will be possible to construct a light rays radiation cloth capable of high light rays density. According to this embodiment, it will also be clear that the light rays can be guided into the optical fiber from both end portions thereof; or the surface of the basic sheet plate 1, on which the optical fiber 2 are arranged, can be used as a reflecting surface.

Figure 4:
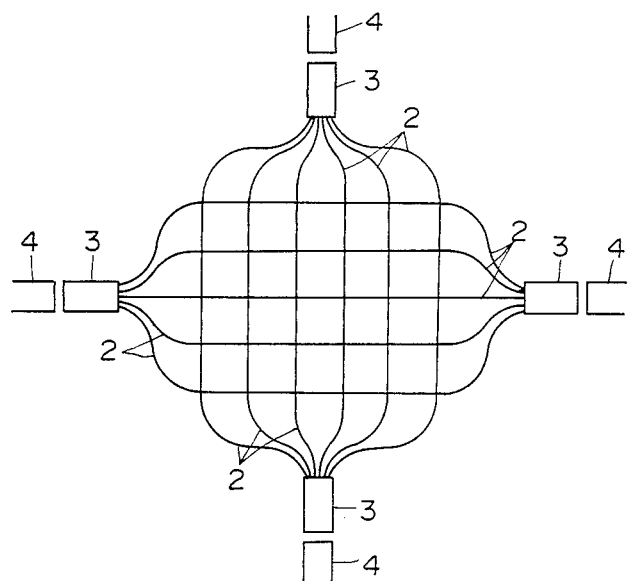

FIG. 4 is a construction view for explaining still another embodiment of the present invention. In this embodiment, a textile is constructed by causing the optical fibers 2 to intersect each other in lengthwise and lateral directions and, the basic sheet plate employed in the former embodiments, is omitted so that the total weight of the radiation cloth can be decreased and its flexibility can be improved.

Figure 5:
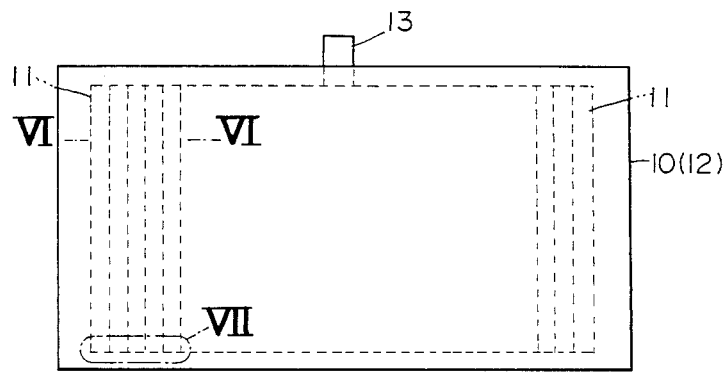
Figure 6A:
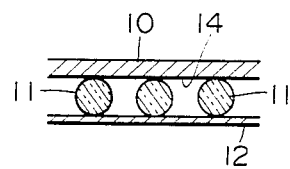
FIGS. 6(A) through 6(C) are respectively enlarged cross-sectional views taken along the line VI—VI of FIG. 5.
Figure 6B:
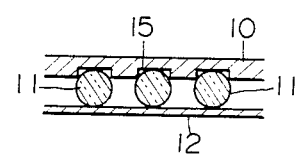
Figure 6C:
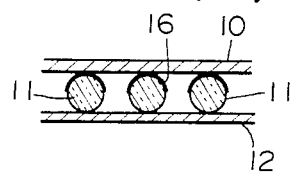

FIG. 5 is a plan view showing still another embodiment of the light rays radiation cloth for medical treatment according to the present invention. FIGS. 6(A) through 6(C) are respectively enlarged, cross-sectional views, taken along the line VI—VI of FIG. 5. In those figures, 10 is a flexible basic sheet plate, 11 an optical fiber, 12 a transparent flexible basic sheet plate, and 13 a light rays connector. As shown in FIG. 5, a large number of optical fibers 11 are arranged so as to be held together in parallel with each other in a space between the flexible basic sheet plate 10 and the transparent flexible basic sheet plate 12.

As is apparent from the foregoing description, it may be shown that the light rays radiation cloth for medical treatment, according to the present invention, radiates the light rays only from one surface. Therefore, the relationship between the basic sheet plates, 10 and 12, and the optical fibers 11 is established as shown in FIGS. 6(A) through 6(C), for example. And further, the basic sheet plates and the optical fibers are bonded to each other by use of an adhesive such as optical paste and thereby the position of the respective optical fibers doesn't deviate at all.

In the embodiment shown in FIG. 6(A), a reflecting membrane 14 consisting of a titanic oxide membrane is formed on the surface of the basic sheet plate 10. By bringing the titanic oxide membrane 14 into contact with the optical fiber, the light rays transmitted through the optical fiber 11 are dispersed. In such a manner, the dispersing light rays are emitted outside of the optical fiber 11 through the transparent basic sheet plate 12 employed for protecting it.

In the embodiment shown in FIG. 6(B), a large number of notched grooves 15 used for positioning the optical fibers 11 thereon are formed parallel to each other on the surface of the basic sheet plate 10, and the optical fibers 11 are arranged along the grooves 15. Moreover, the entire surface of the basic sheet plate 10 is coated with a titanic oxide membrane 14 or only the surface in the notched groove 15 is coated with the titanic oxide membrane 14. Otherwise, as shown in FIG. 6(C), only the surface of the optical fiber 11 is coated with the titanic oxide membrane 14.

In the embodiment shown in FIG. 6(C), the surface of the optical fiber 11, at the side coming into contact with the basic sheet plate 10, is coated with the titanic oxide membrane 16. The light rays transmitted through the optical fiber 11 are dispersed by means of the titanic oxide membrane 16. The embodiment in which the entire contact surface of the optical fiber 11 and the basic sheet plate 10 is coated with the titanic oxide membrane 14 has been described heretofore. However, the contact surface thereof may be coated intermittently in order to make the light rays emitting portion uneven i.e. irregular.

Figure 7:
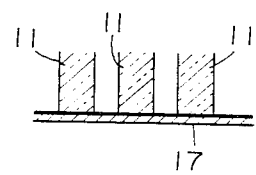
FIG. 7 is an enlarged view showing the portion encircled by the line VII of FIG. 5.

FIG. 7 is an enlarged view showing the portion encircled by the line VII of FIG. 5. The end portion of the respective optical fibers 11 comes into contact with a reflecting plate 17. Thereby, the remaining light rays transmitted through the optical fiber 11 are reflected on to the reflecting plate 17 and transmitted back in the opposite direction in order to disperse the light rays that are on the return route. In such a manner as mentioned heretofore, it is possible to improve the utility of the light rays. As a matter of course, it can easily be understood that the end portion of the respective optical fibers 11 may be individually processed to form a reflecting surface.

According to the present invention, since the radiation cloth is constructed so as to radiate the light rays from one surface of the optical fiber as mentioned above, a waist-band, an arm-band, a leg-band, a head-band, or the like can be constructed by employing the afore-mentioned radiation cloth.

The light rays are radiated on to the specified portion of the human body bound by the radiation cloth in order to administer medical treatment or to promote the health of a person. Otherwise, the radiation cloth is put on top of footwear, such as a slipper, in order to radiate the light rays onto the rear side of the foot, or the inner side of a large container can be covered with the radiation cloth as a lining for the purpose of giving a light rays-bath inside the container as for example a capsule. Furthermore, the radiation cloth can mounted on the inner side of clothing as a shawl, a waistcoat (vest), a bathrobe, a poncho, or the like for the person wearing the above-mentioned clothing to receive a light rays-bath.

As is apparent from the foregoing description, according to the present invention, a light rays radiation cloth for emitting the light rays from one surface thereof and for radiating the same onto a desired portion of the human body can be mechanically processed and assembled in a desired form and structure and can be employed to administer medical treatments for the diseased parts of a human body or to promote the general health of a person.

I claim:

1. A light rays radiation cloth for emitting light rays from only one surface for medical treatment comprising a flexible basic sheet and a flexible transparent sheet spaced from said basic sheet, a plurality of optical fiber means disposed between said basic sheet and said transparent sheet, a light rays connector for supplying light rays to said optical fiber means, said optical fiber means being in contact with said transparent sheet, said optical fiber means being spaced from said basic sheet, and a titanic oxide membrane disposed between said optical fiber means and said basic sheet such that said titanic oxide membrane precludes light rays emitted by said optical fiber means from passing outwardly through said basic sheet as said light rays emitted from said optical fiber means are dispersed by said titanic oxide membrane to pass outwardly of the radiation cloth through said transparent sheet.

2. A light rays radiation cloth according to claim 1, wherein the surface of said basic sheet juxtaposed to said optical fiber means is coated with said titanic oxide membrane.

3. A light rays radiation cloth according to claim 1, wherein said optical fiber means comprises a plurality of parallel fibers.

4. A light rays radiation cloth according to claim 3, wherein said basic sheet comprises a plurality of parallel grooves, said fibers being disposed in said grooves.

5. A light rays radiation cloth according to claim 4, wherein said grooves are coated with said titanic oxide membrane.

6. A light rays radiation cloth according to claim 5, wherein the entire surface of said basic sheet in which said grooves are formed is coated with said titanic oxide membrane.

7. A light rays radiation cloth according to claim 3, wherein said fibers have one surface facing and juxtaposed to said basic sheet and another surface facing and juxtaposed to said transparent sheet, said one surface being coated with said titanic oxide membrane, and optical paste bonding said other surface directly to said transparent sheet.

8. A light rays radiation cloth according to claim 7 further comprising bonding means bonding said coated one surface of said optical fibers to said basic sheet.

9. A light rays radiation cloth according to claim 3, wherein said parallel fibers have one longitudinal end leading to said connector and reflecting means on the other longitudinal ends of said parallel fibers operable to reflect and transmit light rays back into the respective fibers.

10. A light rays radiation cloth according to claim 9, wherein said reflecting means comprises a reflecting plate in contact with said other longitudinal ends of said parallel fibers.

11. A light rays radiation cloth according to claim 1, wherein said basic sheet comprises a textile material.

12. A light rays radiation cloth according to claim 1, wherein said basic sheet comprises cloth.

13. A light rays radiation cloth for emitting light rays from only one surface for medical treatment comprising a flexible basic material and a flexible transparent material spaced from said basic material, a plurality of parallel optical fibers disposed between said basic material and said transparent material, a light rays connector connected to one longitudinal end of said plurality of parallel fibers for supplying light rays to one longitudinal end of each of said parallel optical fibers, reflecting means on the other longitudinal ends of said parallel fibers operable to reflect and transmit light rays back into the respective fiber in a direction toward said connector, each of said parallel fibers having one surface facing and juxtaposed to said basic material and another opposite surface facing and juxtaposed to said transparent material, optical paste means bonding said other surface to said transparent material, said one surface being spaced from said basic material, a titanic oxide membrane disposed between said one surface and said basic material such that said titanic oxide membrane precludes light rays emitted by said parallel optical fibers from passing outwardly through said basic material as said light rays emitted from said parallel optical fibers are dispersed by said titanic oxide membrane to pass outwardly of the radiation cloth through said transparent material, and bonding means bonding said coated one surface of said optical fibers to said basic material.

14. The combination comprising an item of clothing and a light radiation cloth affixed to said item of clothing for providing a light rays bath to a person wearing said clothing, said light radiation cloth comprising a flexible basic material and a flexible transparent material spaced from said basic material, a plurality of parallel optical fibers disposed between said basic material and said transparent material, a light rays connector connected to one longitudinal end of said plurality of parallel fibers for supplying light rays to one longitudinal end of each of said parallel optical fibers, reflecting means on the other longitudinal ends of said parallel fibers operable to reflect and transmit light rays back into the respective fiber in a direction toward said connector, each of said parallel fibers having one surface facing and juxtaposed to said basic material and another opposite surface facing and juxtaposed to said transparent material, optical paste means bonding said other surface to said transparent material, said one surface being spaced from said basic material, a titanic oxide membrane disposed between said one surface and said basic material such that said titanic oxide membrane precludes light rays emitted by said parallel optical fibers from passing outwardly through said basic material as said light rays emitted from said parallel optical fibers are dispersed by said titanic oxide membrane to pass outwardly of the radiation cloth through said transparent material, and bonding means bonding said coated one surface of said optical fibers to said basic material, said radiation cloth being affixed to said item of clothing such that a person wearing said item of clothing receives a light-bath from said radiation cloth.

* * * * *